United States Patent [19]

Freitag et al.

[11] 4,308,216

[45] Dec. 29, 1981

[54] PROCESS FOR THE PREPARATION OF AROMATIC DICARBOXYLIC ACID DICHLORIDES

[75] Inventors: Dieter Freitag, Krefeld, Fed. Rep. of Germany; Manfred Schmidt, New Martinsville, W. Va.; Ludwig Bottenbruch, Krefeld, Fed. Rep. of Germany

[73] Assignee: Bayer Aktiengesellschaft, Fed. Rep. of Germany

[21] Appl. No.: 164,046

[22] Filed: Jun. 30, 1980

[30] Foreign Application Priority Data

Aug. 16, 1979 [DE] Fed. Rep. of Germany ....... 2933148

[51] Int. Cl.$^3$ .............................................. C07C 51/60
[52] U.S. Cl. ................................................ 260/544 K
[58] Field of Search ..................................... 260/544 K

[56] References Cited

U.S. PATENT DOCUMENTS

2,657,233 10/1953 Carnahan ......................... 260/544 K
3,962,326 6/1976 Semler et al. .................... 260/544 K

OTHER PUBLICATIONS

Lee, John B., *J. Am. Chemical Society*, vol. 88 (1966), pp. 3440-3441.
Kosolapoff, Gennady M., "Organophosphorus Compounds", (1959), John Wiley & Sons, Publ., pp. 98-101.

*Primary Examiner*—Natalie Trousof
*Assistant Examiner*—Leah Hendriksen
*Attorney, Agent, or Firm*—Connolly and Hutz

[57] ABSTRACT

A one-step process for the preparation of pure aromatic dicarboxylic acid dichlorides by reacting an aromatic dicarboxylic acid or an aromatic dicarboxylic acid mixture with phosgene in the presence of a catalyst and, optionally, in a solvent or diluent, by using tertiary phosphines as catalysts, and the use of the dicarboxylic acid dichlorides obtained for the production of polycondensates.

4 Claims, No Drawings

PROCESS FOR THE PREPARATION OF AROMATIC DICARBOXYLIC ACID DICHLORIDES

This invention relates to a one-step process for the preparation of very pure aromatic dicarboxylic acid dichlorides capable of polycondensation.

The production of aliphatic and aromatic acid chlorides by reacting a carboxylic acid with phosgene is described in U.S. Pat. Nos. 3,184,506; 3,544,626; 3,544,627; 3,547,960 and also in German Offenlegungsschrifts Nos. 2,400,007 and 2,321,122. By these processes, darkly coloured carboxylic acid chlorides are obtained as the reaction products in a purity of from 96 to 99%. Aromatic dicarboxylic acid chlorides having this low purity level cannot be used directly in the two-phase interface polycondensation process for the preparation of high-molecular-weight polycondensates, such as aromatic polyamides or aromatic polyesters. Their content of unreacted or only half reacted dicarboxylic acids disturbs the polycondensation process, causes undesirable breaks in the chain and produces polymers having terminally-positioned carboxyl groups. The aromatic dicaroxylic acid dichlorides prepared in this way have a dark colour owing to the presence of impurities and contain disturbing carbamic acid chlorides produced as a result of the reaction with the catalysts (compare Chem. Ref. 1973, Vol 73, No 1 page 77 or Angewandte Chemie (1974), Vol. 1962, No. 21, page 864).

In order to obtain colourless dicarboxylic acid dichlorides, the crude products have to be purified by recrystallisation or distillation. This necessitates additional complexity and decreases the yield; there is a danger with aromatic dicarboxylic acid dichlorides that they could decompose spontaneously.

The present invention provides a one-step process for the preparation of pure aromatic dicarboxylic acid dichlorides by reacting aromatic dicarboxylic acids with phosgene in the presence of a catalyst and, optionally, in a solvent and/or diluent, wherein tertiary phosphines are used as catalysts.

The aromatic dicarboxylic acid dichlorides thus obtained are practically colourless, and besides containing the used catalysts, they also contain 0.1% or less of impurities so that they can be used for the preparation of colourless high-molecular-weight polycondensates without needing to be subsequently purified.

The tertiary phosphines used according to the invention as catalysts do not, for example, disturb the preparation of aromatic polyesters. The used catalysts can be removed from the reaction mixture by simply commencing to distill this mixture after the reaction has finished. However, the residual remnants of the catalyst in the obtained dicarboxylic acid dichloride do not disturb the conversion of these dicarboxylic acid dichlorides into, for example, aromatic polyesters by the process of two-phase interface reaction, as they are also simultaneously effective transesterification catalyst for this polycondensation reaction.

Tertiary phosphines of the general formula (I) are suitable as active catalysts of the invention:

(I)

wherein $R_1$, $R_2$, and $R_3$ are the same or different and may be $C_1$–$C_8$-alkyl, $C_6$–$C_{10}$-aryl, $C_7$–$C_{20}$-alkylaryl or arylalkyl. $R_1$, $R_2$ and $R_3$ are preferably $C_6$–$C_{10}$-aryl radicals such as phenyl or phenyl substituted by $C_1$–$C_4$-alkyl radicals.

Suitable catalysts are: tribenzylphosphine, triisopropylphosphine, and tributylphosphine. Particularly suitable is triphenylphosphine.

According to the invention, from 0.1 to 3.0% by weight and preferably from 0.2 to 1.5% by weight of tertiary phosphines of the general structure (I) are used, based on the aromatic dicarboxylic acids used.

Aromatic dicarboxylic acids correspond to the following formulae:

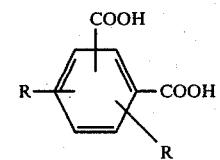
(II)

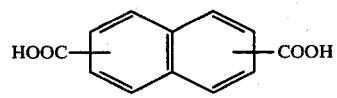
(III)

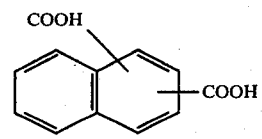
(IV)

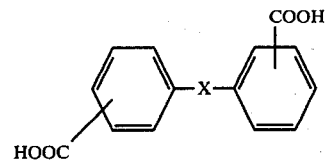
(V)

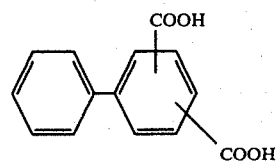
(VI)

Where
R=H, $C_1$–$C_4$-alkyl or halogen (preferably chlorine or bromine),
X=a single bond, —O—, —S—, —CH$_2$—,

$C_5$–$C_7$-cycloalkylene.

Mixtures can also be used. The following are mentioned by way of example: phthalic acid, isophthalic acid, terephthalic acid, mixtures of iso- and terephthalic acid, diphenic acid, and 1,4-naphthalene dicarboxylic acid. As solvents or diluents, it is preferable to use that or those (in the case of mixtures) aromatic dicarboxylic acid dichlorides formed during reaction. Also, benzoyl chloride is suitable as solvent. Inert diluents like, e.g., aliphatic or aromatic hydrocarbons, halogen-substituted aromatic hydrocarbons, halogen-substituted aliphatic hydrocarbons or saturated aliphatic esters can also be used or additionally be used. The reaction temperature is, generally, from 70° to 200° C., preferably from 100° to 180° C.

To carry out the process of the invention in the presence of aromatic dicarboxylic dichlorides, after adding the catalysts of the invention, the aromatic dicarboxylic acids can be suspended or dissolved at from 140° to 180° C. in from 8 to 80% by weight, based on the total reaction mixture, of the corresponding aromatic dicarboxylic acid dichlorides prepared previously, and are then reacted with phosgene at from 70° to 200° C., preferably at from 100° to 180° C.

The molar ratio of aromatic dicarboxylic acid to phosgene is preferably from 1:2 to 1:2.5, i.e., a small excess quantity of phosgene is advisable to replace losses to result during phosgenation when $CO_2$ and HCl gas are released from the reaction mixture.

The process of the invention can be carried out discontinuously or continuously. In a continuous method, a solution heated to from 120° to 180° C. of aromatic dicarboxylic acid, dicarboxylic acid dichloride and catalyst is allowed to flow downwards in a reaction tube against upwards-flowing phosgene gas, and aromatic dicarboxylic acid dichloride and catalysts are collected at the base of the reaction tube.

In a discontinuous method, aromatic dicarboxylic acid, aromatic dicarboxylic acid dichloride and catalyst are introduced under normal pressure at higher temperatures, optionally, under pressure. This mixture is then heated to from 140° to 180° C. with whereby the aromatic dicarboxylic acid is completely or partially dissolved with the evolution of HCl and the formation of anhydride. At this temperature, from 2 to 2.5 moles of gaseous phosgene are introduced per mole of aromatic dicarboxylic acid.

After removing the excess phosgene, the HCl and $CO_2$ gas by applying a vacuum for a short time, a residue is obtained which, besides the quantity of catalyst used, consists to $\geq 99.9\%$ of aromatic dicarboxylic acid dichloride, and which, without being subsequently purified, can be converted into high-molecular-weight, colourless polycondensates.

EXAMPLE 1

The following substances were introduced and heated in a 250 ml flask fitted with a magnetic stirrer, a thermometer, a gas introduction frit and two intensive condensers (from −10° C. to −20° C.) positioned one above the other:

66.4 g of isophthalic acid dichloride,
66.4 g of terephthalic acid dichloride,
16.6 g (0.1 mol) of isophthalic acid,
16.6 g (0.1 mol) of terephthalic acid,
0.166 g of triphenylphosphine ($\triangleq 0.5\%$ by weight, based on the acids).

The pale yellow suspension (>50° C.) is heated to 178° C. for 30 minutes, whereby HCl evolves. After 1 hour at from 178° to 181° C. the HCl evolution, which has been steady up to this time, abates and the mixture is in solution except for a small residual quantity of acids.

Nitrogen is then passed through the reaction mixture for 30 minutes. As a result of this, the residual quantity of acids passes *rapidly* into solution.

Phosgene is introduced into this clear pale yellow solution for 45 minutes at from 180° to 184° C. Thereby, $CO_2$ escapes via the condensors, taking with it traces of phosgene. These traces are removed from the mixture in a condensation trap. As a safety measure, a tower filled with active carbon is connected downstream of the condensation trap in order to eliminate residual traces of phosgene. After introducing phosgene for 45 minutes, the solution is clear and the temperature drops from 184° C. to 176° C., depending on the phosgene reflux. The phosgenation process is completed. In order to remove the excess phosgene, cooling is switched off, flushing is carried out with $N_2$ and distillation is effected at 148° C. under decreased pressure for 10 minutes.

The residue contains
$\geq 99.9\%$ of acid chlorides,
$<0.1\%$ of COOH,
$<0.05\%$ of HCl.

An aromatic polyester having an $\eta$ rel value of 1.291 was prepared using these acids chlorides and bisphenol A, in the presence of 3 mol % of tertiary-butyl phenol as chain breaker, according to the conventional interface polycondensation process.

EXAMPLE 2

203 g (1 mol) of isophthalic acid dichloride, 166 g of isophthalic acid (1 mol) and 0.8 g of triphenyl phosphine are heated to 148° C. in a round flask, fitted with a thermometer, a stirrer and an intensive condenser maintained at −20° C. by cooling brine. At from 148° to 157° C., phosgene is introduced with stirring and reflux boiling until the temperature of the reaction mixture drops to 146° C.

After cooling to 120° C., a water jet vacuum is applied, whereby excess phosgene and HCl and $CO_2$ gas dissolved in the reaction mixture are removed.

Yield: 406.2 of a colourless residue which consists of 0.3 g of the catalyst used and 405.9 g of a 100% isophthalic acid dichloride (determined titrimetrically).

EXAMPLE 3

101.5 g (0.5 mol) of isophthalic acid dichloride, 101.5 g (0.5 mol) of terephthalic acid dichloride, 83 g (0.5 mol) of isophthalic acid, 83 g (0.5 mol) of terephthalic acid and 0.8 g of triphenyl phosphine are reacted with phosgene, as described in Example 1.

Yield: 406.3 g of a colourless residue which consists of 0.3 g of the catalyst used and 406 g of a mixture of 100% iso and terephthalic acid dichloride (determined titrimetrically).

EXAMPLE 4

101.5 g (0.5 mol) of isophthalic acid dichloride, 101.5 g (0.5 mol) of terephthalic acid dichloride, 83 g (0.5 mol) of isophthalic acid, 83 g (0.5 mol) of terephthalic acid and 0.8 g of tributyl phosphine are reacted with phosgene, as described in Example 1.

Yield: 406.4 g of 99.9% iso and terephthalic acid dichloride, which contains 0.4 g of the catalyst used.

EXAMPLE 5

101.5 g (0.5 mol) of isophthalic acid dichloride, 101.5 g (0.5 mol) of terephthalic acid dichloride, 83 g (0.5 mol) of isophthalic acid, 83 g (0.5 mol) of terephthalic acid and 0.6 g of tribenzyl phosphine are reacted with phosgene, as described in Example 1.

Yield: 406.4 g of a practically colourless residue consisting of 99.9% iso and terephthalic acid dichloride (determined titrimetrically) and 0.4 g of the catalyst used.

We claim:

1. A process for preparing aromatic dicarboxylic acid dichloride which comprises reacting an aromatic dicarboxylic acid selected from the group consisting of

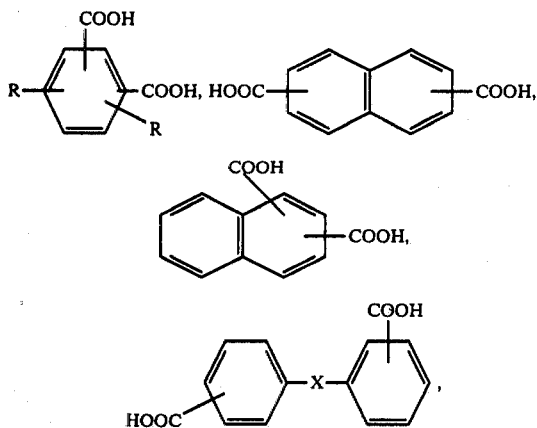

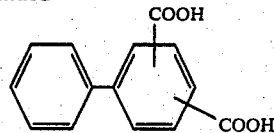

and mixtures thereof wherein
R is H, $C_1$-$C_4$-alkyl or halogen and
X is a single bond, —O—, —S—, —$CH_2$—,

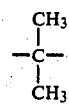

or $C_5$-$C_7$ cycloalkylene
with phosgene in the presence of a catalytic amount of a tertiary phosphine of the formula

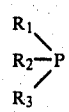

wherein $R_1$, $R_2$ and $R_3$ are each selected from the group consisting of $C_1$-$C_8$ alkyl, $C_6$-$C_{10}$ aryl, $C_7$-$C_{20}$ aralkyl and $C_7$-$C_{20}$ aralkyl.

2. A process of claim 1 wherein said reaction is carried out in the presence of a diluent.

3. A process of claim 1 wherein $R_1$, $R_2$ and $R_3$ are each $C_6$-$C_{10}$ aryl.

4. A process of claim 1 wherein $R_1$, $R_2$ and $R_3$ are each phenyl or phenyl substituted by $C_1$-$C_4$ alkyl.

* * * * *